United States Patent
Runco et al.

(10) Patent No.: US 7,572,281 B2
(45) Date of Patent: Aug. 11, 2009

(54) INSTRUMENT FOR GUIDING A ROD INTO AN IMPLANT IN A SPINAL FIXATION SYSTEM

(75) Inventors: Thomas J. Runco, Canton, MA (US); Ronald Garner, Hull, MA (US)

(73) Assignee: DePuy Spine, Inc., Raynham, MA (US)

( * ) Notice: Subject to any disclaimer, the term of this patent is extended or adjusted under 35 U.S.C. 154(b) by 736 days.

(21) Appl. No.: 10/913,223

(22) Filed: Aug. 6, 2004

(65) Prior Publication Data

US 2006/0036260 A1 Feb. 16, 2006

(51) Int. Cl.
*A61B 17/70* (2006.01)

(52) U.S. Cl. .......................... 606/279; 606/246; 606/99

(58) Field of Classification Search ................... 606/61, 606/73, 99, 104, 246, 250, 264, 265, 272, 606/277, 278, 279, 301, 305, 308, 86 A
See application file for complete search history.

(56) References Cited

U.S. PATENT DOCUMENTS

| | | | |
|---|---|---|---|
| 5,020,519 A | 6/1991 | Hayes et al. |
| 5,364,397 A | 11/1994 | Hayes et al. |
| 5,720,751 A | 2/1998 | Jackson |
| 5,782,831 A | 7/1998 | Sherman et al. |
| 5,910,141 A | 6/1999 | Morrison et al. |
| 6,123,707 A | 9/2000 | Wagner |
| 6,183,472 B1 | 2/2001 | Lutz |
| 6,440,133 B1 | 8/2002 | Beale et al. |
| 6,511,484 B2 | 1/2003 | Torode et al. |
| 6,648,888 B1 | 11/2003 | Shluzas |
| 6,660,006 B2 | 12/2003 | Markworth et al. |
| 6,743,231 B1 | 6/2004 | Gray et al. |
| 2002/0095153 A1 | 7/2002 | Jones et al. |
| 2003/0028195 A1 | 2/2003 | Bette |
| 2003/0199872 A1 | 10/2003 | Markworth et al. |
| 2003/0225408 A1 | 12/2003 | Nichols et al. |
| 2004/0049191 A1 | 3/2004 | Markworth et al. |

FOREIGN PATENT DOCUMENTS

DE 4238339 A1 5/1994

*Primary Examiner*—Eduardo C Robert
*Assistant Examiner*—David Comstock
(74) *Attorney, Agent, or Firm*—Lahive & Cockfield, LLP; Kevin J. Canning

(57) ABSTRACT

An instrument for guiding a spinal rod into a rod-receiving portion of an implant comprises a linear portion comprising two relatively moveable shafts, an actuator portion coupled to the linear portion for moving the spinal rod relative to the implant and a handle portion for moving the shafts to actuate the actuator portion. The actuator portion holds the rod in place until the surgeon inserts a setscrew or other device for securing the rod to the anchor. The actuator portion further defines a path for inserting and securing a locking device, such as a setscrew, for securing the rod in the implant while also holding the rod in the implant. The path for the screw is aligned with the rod-holding portion of the implant. Using the instrument, a surgeon can guide a rod into a selected position in the implant, reposition the spine to match the contour of the rod, hold the rod in the selected position and secure the rod to the implant.

4 Claims, 15 Drawing Sheets

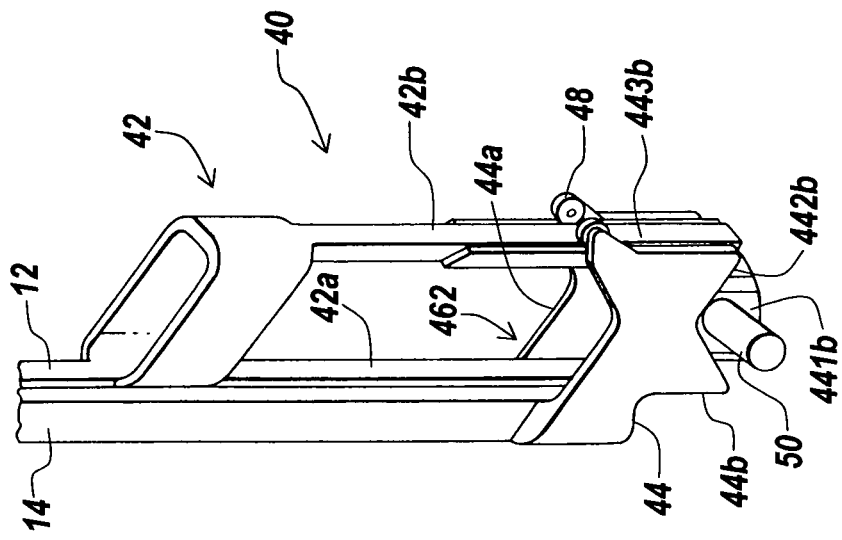
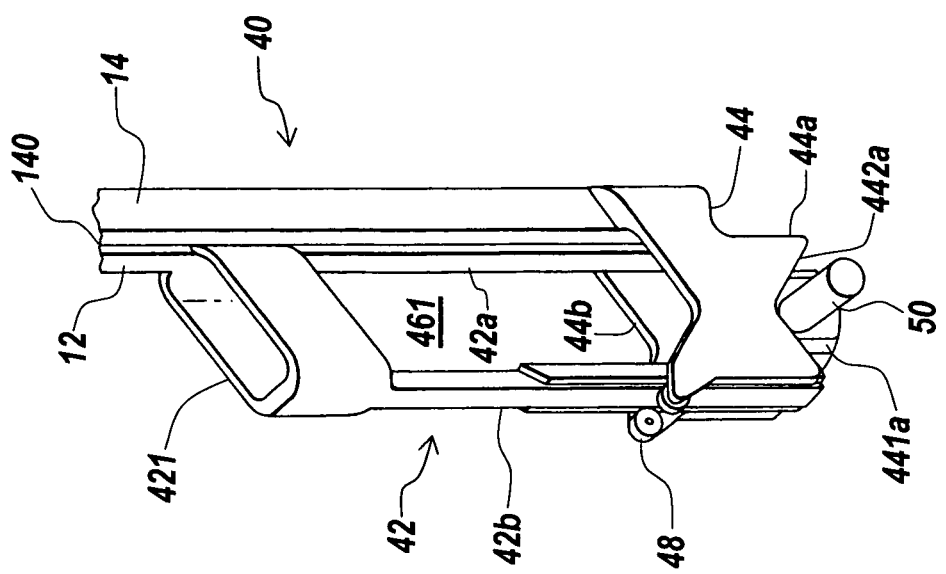
Fig. 2B
Fig. 2A

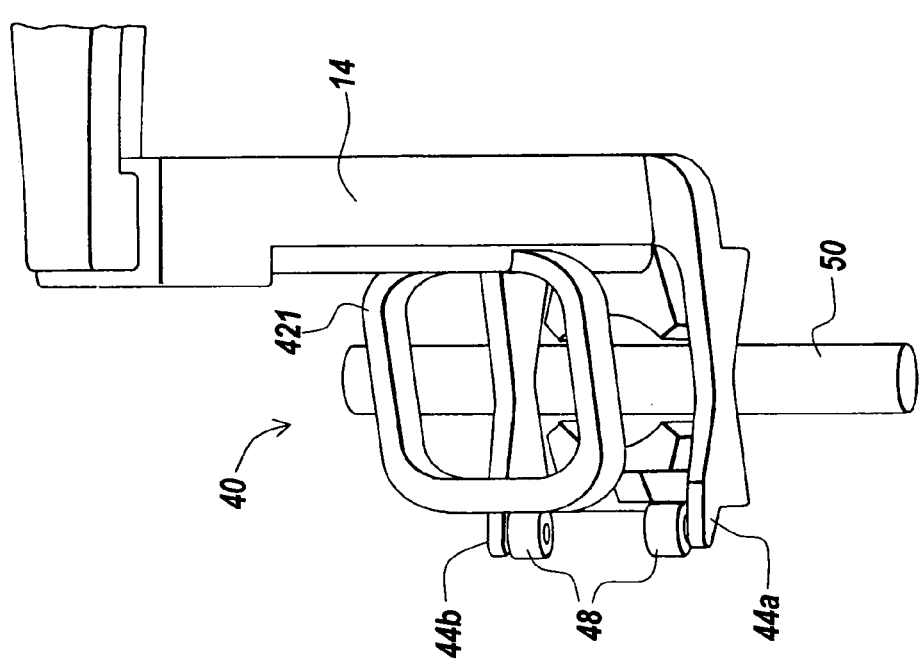
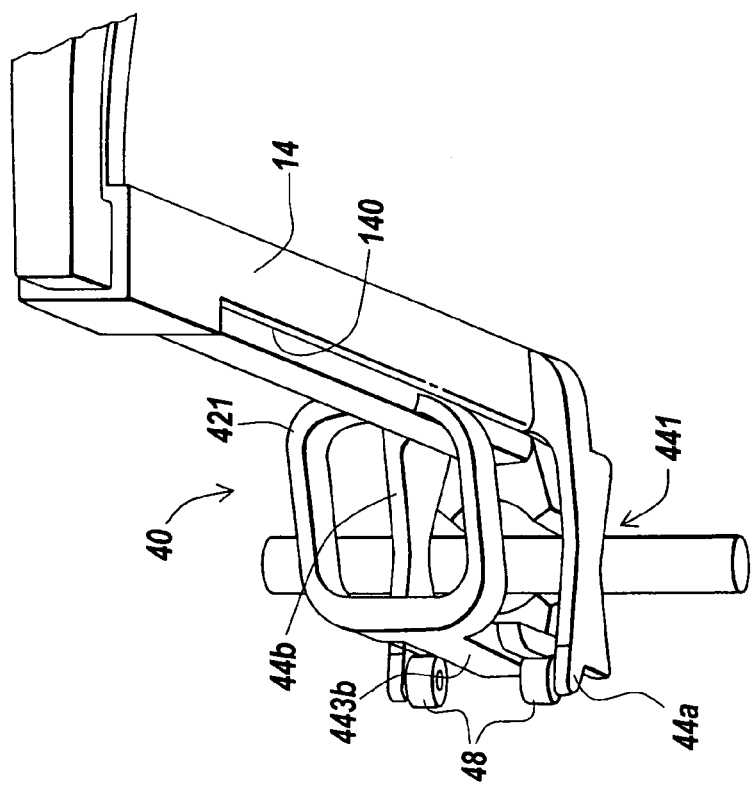
Fig. 2D
Fig. 2C

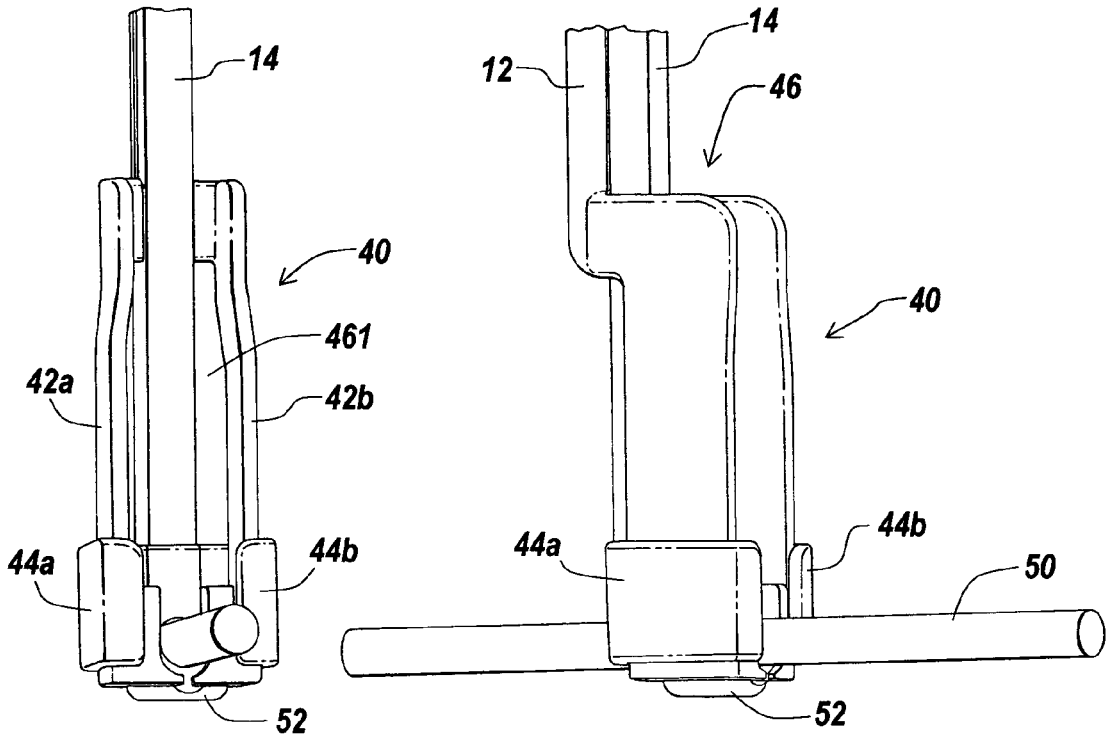
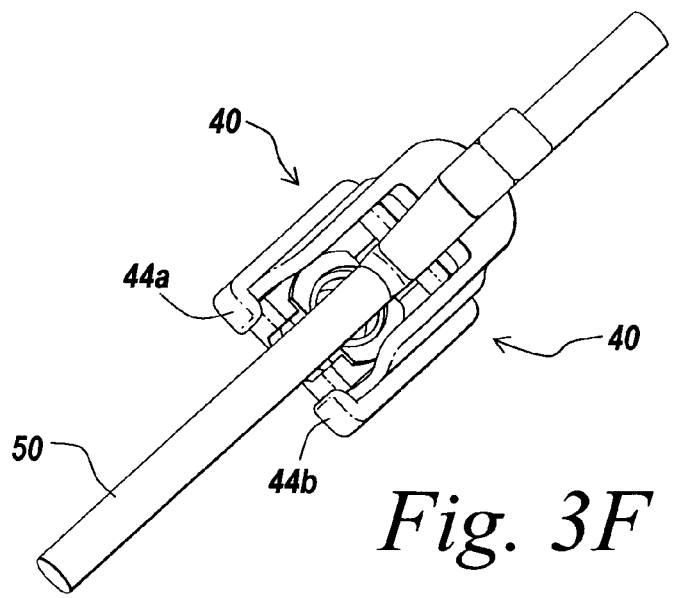

INSTRUMENT FOR GUIDING A ROD INTO AN IMPLANT IN A SPINAL FIXATION SYSTEM

FIELD OF THE INVENTION

The present invention relates to spinal fixation devices used in orthopedic surgery. More particularly, the present invention relates to an instrument for inserting, adjusting and removing a spinal implant, such as a polyaxial pedicle screw.

BACKGROUND OF THE INVENTION

Spinal fixation systems may be used in surgery to align, adjust and/or fix portions of the spinal column, i.e., vertebrae, in a desired spatial relationship relative to each other. Many spinal fixation systems employ a spinal rod for supporting the spine and for properly positioning components of the spine for various treatment purposes. Vertebral anchors, comprising pins, bolts, screws, and hooks, engage the vertebrae and connect the supporting rod to different vertebrae. The size, length and shape of the cylindrical rod depend on the size, number and position of the vertebrae to be held in a desired spatial relationship relative to each other by the apparatus.

During spinal surgery, a surgeon first exposes the spine posterior and attaches the vertebral anchors to selected vertebrae of the spine. The surgeon then inserts a properly shaped spinal rod into rod-receiving portions of the vertebral anchors to connect the selected vertebrae, thereby fixing the relative positions of the vertebrae. Generally, a controlled mechanical force is required to bring together the spinal rod and a spinal implant, such as the vertebral anchors, in a convenient manner. After insertion, a surgeon must insert a locking mechanism, such as a set screw, into the vertebral anchor to lock the spinal rod to the implant after the force for inserting the rod is removed.

There are currently various devices designed and used for reduction of a spinal rod into a vertebral anchor or other spinal implant, which have significant drawbacks. Drawbacks include difficultly generating the amount of force required to insert a spinal rod into implant, difficulty of aligning the rod to the rod-receiving portion of an implant and the lack of direct tactile feedback to the hand of the surgeon. In addition, many devices for coupling a spinal rod and a vertebral anchor include many complex parts and can be difficult or complex to operate.

For example, U.S. Pat. No. 6,660,006 is directed to a rod reduction device including a body releasably attached to an orthopedic device, a pusher member and a trigger slidably coupling the pusher member to the body. The rod reduction device described in U.S. Pat. No. 6,660,006 includes a channel for inserting a fastener extending through the entire body of the instrument. The inter-body channel increases the size and complexity of the rod reduction device. In addition, the location of the channel within the body blocks the channel from view and inhibits access to the channel.

SUMMARY OF THE INVENTION

The present invention provides an instrument and method for guiding a spinal rod into an orthopedic implant. The instrument may be held and operated using one hand, thereby facilitating insertion and securing of a spinal rod in a selected position. The instrument includes a linear portion comprising two relatively moveable shafts, an actuator portion offset from and coupled to the linear portion for moving the spinal rod relative to the implant and a handle portion for moving the shafts to actuate the actuator portion. The actuator portion holds the rod in place until the surgeon inserts a set screw or other device for securing the rod to the anchor. The actuator portion further defines a path for inserting and securing a locking device, such as a set screw, for securing the rod in the implant while also holding the rod in the implant. The path for the screw is aligned with the rod-holding portion of the implant. Using the instrument, a surgeon can guide a rod into a selected position in the implant, reposition the spine to match the contour of the rod, hold the rod in the selected position and secure the rod to the implant.

According to a first aspect of the invention, an instrument for guiding a spinal rod into an implant is provided. The instrument comprises a first shaft, a second shaft coupled to and slidable relative to the first shaft, such that the first and second shaft extend substantially parallel to each other, an actuator coupled to the first shaft and the second shaft for guiding the spinal rod into a rod-receiving portion of the implant and a channel extending through the actuator portion. The channel defines a path for inserting a locking mechanism to lock the spinal rod into the rod-receiving portion.

According to another aspect of the invention, an instrument for guiding a spinal rod into an implant comprises a first handle and a second handle pivotally coupled to the first handle at a first hinge point. The instrument further includes a first shaft coupled to the first handle and a second shaft slidably coupled to the first shaft and pivotally coupled to the second handle at a second hinge point. An implant engagement mechanism is coupled to the first shaft for engaging the implant and a rod reducer is coupled to the second shaft for engaging and guiding the spinal rod into a rod-receiving portion of the implant.

According to yet another aspect of the invention, a method of guiding a spinal rod into an implant comprises the steps of engaging the implant with an implant engagement mechanism coupled to a first shaft, engaging the spinal rod with a rod reducer coupled to a second shaft slidably mated to the first shaft and sliding the first shaft relative to second shaft to cause the rod reducer to push the rod towards a rod-receiving portion of the implant engaged by the implant engagement mechanism.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

FIG. 2a-2d are detailed views of the actuator portion of the instrument of FIG. 1.

FIG. 3a is a front perspective view of an actuator portion of an instrument for inserting a spinal rod into an implant according to another embodiment of the invention when engaging rod, prior to reducing the spinal rod into an implant FIG. 3b is a side view of the actuator portion of FIG. 3a.

FIG. 3c cross-sectional top view of the actuator portion of 3a.

FIG. 3d is a front view of the actuator portion of FIG. 3a when reducing a rod into an implant.

FIG. 3e is a side view of the actuator portion of FIG. 3a.

FIG. 3f is a cross-sectional top view of the actuator portion of FIG. 3a when the rod is reduced in the implant.

DETAILED DESCRIPTION

Figure 1:
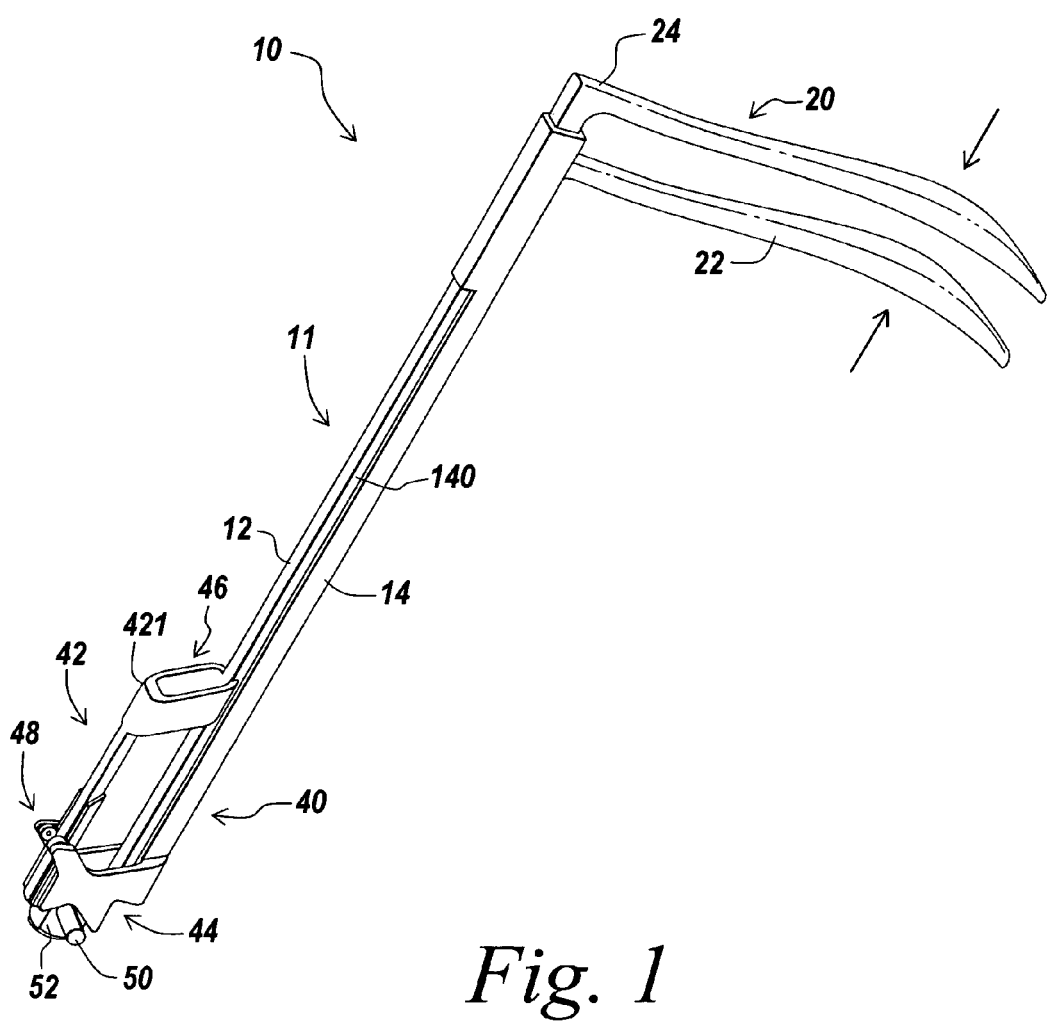
FIG. 1 is a perspective view of an instrument for inserting a spinal rod into an implant according to an illustrative embodiment of the invention.

The present invention provides an improved instrument for inserting a spinal rod into an implant, such as a polyaxial screw, in a spinal fixation system. One skilled in the art will recognize that the invention is not limited to use in spinal surgery and that the instrument and methods described herein can be adapted for use with any suitable surgical device to be moved into a selected position in a variety of medical procedures. The present invention will be described below relative to an illustrative embodiment. Those skilled in the art will appreciate that the present invention may be implemented in a number of different applications and embodiments and is not specifically limited in its application to the particular embodiments depicted herein.

FIGS. 1a-7f illustrate different embodiments of an instrument 10 for inserting a spinal fixation element, such as a spinal rod, into an implant, such as a polyaxial screw, hook or other fastener device used in a spinal fixation system, according to an illustrative embodiment of the invention. The illustrative instrument is configured for engaging and seating a spinal rod in a rod-receiving portion of a polyaxial screw, though one skilled in the art will recognize that the instrument may be used for any suitable surgical device. As shown, the instrument 10 includes linear portion 11 comprising two longitudinally extending shafts 12, 14. The first shaft 12 extends along a longitudinal axis and the second shaft 14 is slidably coupled to and extends substantially parallel to the first shaft 12. The instrument further includes a handle portion 20 at a first end of the instrument 10, i.e., the proximal end relative to a surgeon holding the instrument. The handle portion 20 comprises a first handle 22 and a second handle 24 configured to be received in the hand of the surgeon. The first handle 22 extends from a first end of the first shaft 12 and a second handle 24 extends from a first end of the second shaft 14. Each handle portion 22 or 24 may be integrally formed with the associated shaft or otherwise coupled thereto through any suitable means. The instrument further includes an actuator portion 40 at a second end of the instrument 10, i.e., the distal end, for selectively engaging and inserting a spinal rod into a rod-receiving portion of a selected polyaxial screw or other suitable implant when a user actuates the instrument 10.

According to the illustrative embodiment, the actuator portion 40 is actuated by moving the first shaft 12 relative to the second shaft 14. In the illustrative embodiments, the first shaft 12 and second shaft 14 slide relative to each other by moving the first handle 22 relative to the second handle 24, for example, by holding the handle portion 20 in the palm of the hand and squeezing to bring the handles 22, 24 toward each other. One skilled in the art will recognize that any suitable actuation means may be used.

The shafts 12, 14 may have any suitable size and shape and may be formed on any suitable surgical material, such as titanium, stainless steel and other surgical materials known in the art. In a preferred embodiment, each shaft 12, 14 comprises an elongated, solid, substantially rigid member having a proximal end connected to the handle portion 20 and a distal end connected to the actuator portion 40. The linear portion 11 preferably has a sufficient length so as to enable the distal end to be placed adjacent to a surgical site, while proximal end remains outside the patient's body and accessible by the surgeon.

The shafts 12, 14 may be slidably mated through any suitable means. For example, in the embodiments shown in FIGS. 1-2d, the second shaft 14 includes a recess or channel 140 configured to receive the first shaft 12. The recess or channel constrains the movement of the first shaft 12, such that the first shaft can only move in the direction defined by the longitudinal axis of the instrument relative to the second shaft 14.

Alternatively, one or more pins coupled to one of the shafts can mate with one or more slots on the other shaft limit the amount of relative movement of the shafts, while facilitating sliding of the shafts relative to each other. For example, as shown in FIGS. 5A-5E, the second shaft 14 includes a pin 142 configured to mate with a slot 124 on the first shaft 12. The pin 142 extends through protrusions 143 extending from the second shaft 14 defining a recess for the first shaft 12.

Figure 6:
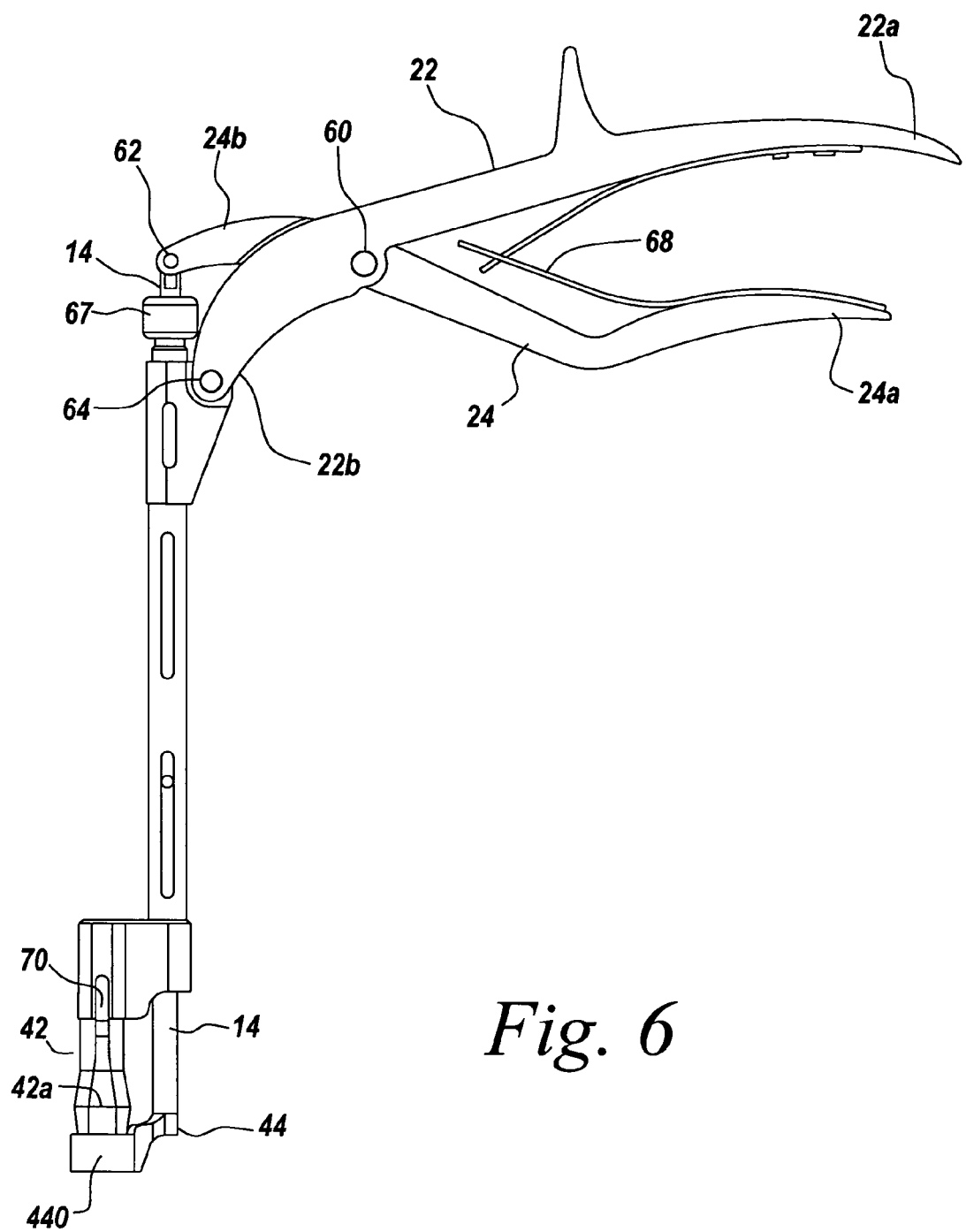
FIG. 6 illustrates an instrument for inserting a spinal rod into an implant including a double hinge to provide additional leverage, according to another embodiment of the invention

In an alternate embodiment of the invention, an example of which is shown in FIG. 6, one of the shafts may comprise a hollow tubular structure configured to slidably receive and constrain the other shaft therein, such that the axes of the shafts align with each other. As shown in FIG. 6, the shaft 12 includes a channel extending therethrough sized and configured to slidably receive the second shaft 14.

The shafts 12, 14 may alternatively be disposed adjacent to each other or spaced apart from each other and slidably coupled together through any suitable means known in the art. One skilled in the art will recognize that any suitable means may be used to slidably couple the first shaft 12 and the second shaft 14.

The actuator portion 40 of the instrument 10 may have any suitable configuration suitable for engaging both the selected implant and a portion of the spinal rod, and moving the engaged portion of the spinal rod into a rod-receiving portion of the implant. The actuator portion 40 includes an implant engagement mechanism 42 coupled to the first shaft 12 for engaging a portion of the selected implant, for example the head of a polyaxial screw. The actuator portion 40 also includes a rod reducer 44 coupled to the second shaft 14 for engaging and applying a force to the spinal rod 50 to reduce the spinal rod into a rod-receiving portion of the implant 52 engaged by the implant engagement mechanism 42. In the illustrative embodiment, the actuator portion 40 is actuated by moving the first shaft 12 relative to the second shaft 14, for example, by squeezing together the handles 22, 24, to move the rod reducer 44 towards the implant engagement mechanism 42. According to the illustrative embodiment, the rod reducer 44 also functions as an implant locking mechanism for selectively locking the engagement mechanism 42 to the implant, as described in detail below.

As shown in FIG. 1, the actuator portion 40 further includes a channel 46 defining a path for inserting and securing a rod-locking mechanism, such as a setscrew, to secure the rod in the implant. The channel 46 allows for a user to secure the rod in the implant after the rod reducer 44 places the rod in a selected position and while maintaining a force on the rod. The channel 46 aligns with the rod reducer 44 and implant-engagement mechanism 42, so that a user can insert a rod-locking mechanism to lock the rod to the implant after insertion along the same path that force is applied to the rod by the rod reducer 44. The channel 46 aligns with the portion of the rod that is inserted into the rod-receiving portion of the implant to allow for a balanced application of force while inserting and securing rod. In this manner, a surgeon can hold the rod in the implant while locking the rod to the implant using a setscrew or other suitable means.

As shown, the actuator portion 40 is preferably offset from the shafts 12, 14, so that the channel 46 defining the path for inserting and securing a rod-locking mechanism extends substantially parallel to and spaced from the longitudinal axis of the shafts 12, 14. The offset position of the actuator portion facilitates the insertion of the rod-locking mechanism by providing access to the path 46 and enhanced visibility of the rod-locking mechanism during insertion. Because the path 46 is external to the shafts 12, 14, the linear portion 11 of the rod can be made more compact.

In use, the rod reducer 44 and implant engagement mechanism 42 of the actuator portion 40 are moveable between a first position, in which the distal end of the rod reducer 44 is spaced from the implant engagement mechanism 42 by a selected distance, and a second position, in which the distal end of the rod reducer 44 is adjacent to or in contact with the implant engagement mechanism 42. After engaging a rod while the instrument is in the first position, the user moves the instrument 10 to the second position to push the rod 05 into a rod-receiving portion of the implant 52. According to one embodiment, the step of moving from the first position to the second position locks the implant-engagement mechanism 42 to the implant.

In the illustrative embodiment, the actuator portion is moved between the first and second positions by moving the handles 22, 24 and corresponding shafts 12, 14 connected to the actuator portion 40 between a first and second position. One skilled in the art will recognize that any suitable means for actuating the instrument may be utilized. According to an illustrative embodiment, in the first position, the handles 22, 24 are separated by a predetermined open distance of between about 50 and about 100 millimeters and preferably about 70 millimeters to sufficiently separate the rod reducer 44 from the implant engagement mechanism 42. In the second position, the handles 22, 24 are separated by a predetermined closed distance of between about 30 millimeters and about 70 millimeters to position the rod reducer 44 and implant engagement mechanism in proximity with each other. One skilled in the art will recognize that the invention is not limited to these ranges and that the handles may be separated in the first and second positions by any suitable distance.

The rod reducer 44 may have any suitable size and configuration suitable for engaging and moving a spinal rod to a selected position when a user slides the shafts 12, 14 relative to each other. In the embodiment shown in FIGS. 1, 2a-2d and 3a-f, the rod reducer 44 comprises substantially parallel protrusions 44a, 44b extending from the distal end of the second shaft 14. The illustrative protrusions 44a, 44b extend substantially perpendicular to the distal end of the second shaft, on the opposite side of the second shaft from the handles 22, 24, though one skilled in the art will recognize that the protrusions 44a, 44b may have any suitable orientation, position and configuration. The protrusions 44a, 44b each include a lower bearing surface 442a, 442b, respectively, defining recesses 441a, 441b, which form a rod seat 441 sized and configured to receive a portion of the rod therein.

In the embodiment of FIGS. 3a-3f the protrusions 44a, 44b are connected by a back wall 44c which defines the rod seat 44a, while in the embodiments of FIGS. 1 and 2a-2d, the protrusions 44a, 44b define the rod seat. One skilled in the art will recognize that the protrusions defining the rod reducer 44 may have any suitable size, shape, orientation and configuration.

Figure 4:
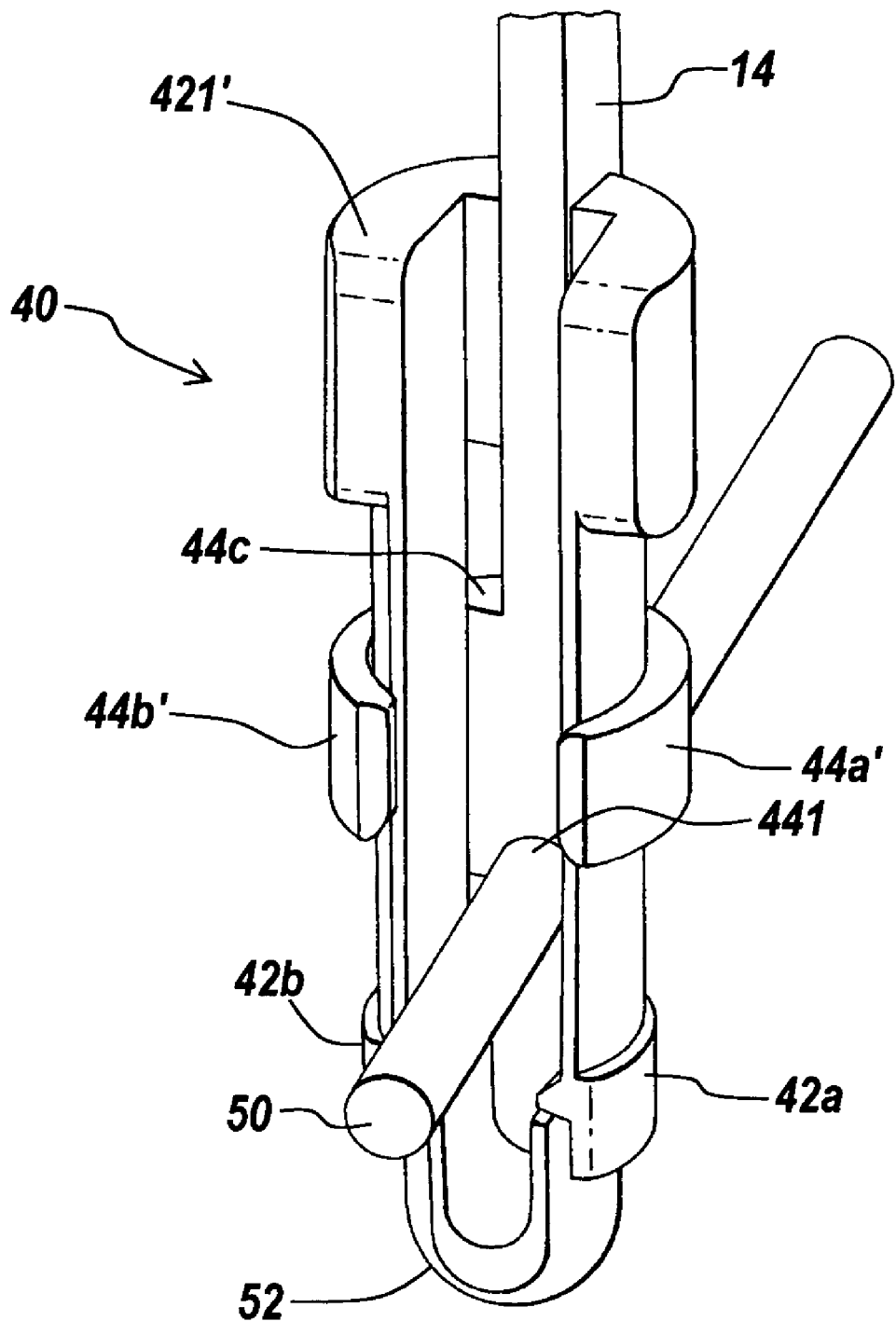
FIG. 4 illustrates an embodiment of an actuator portion of an instrument for inserting a spinal rod into an implant according to another embodiment of the invention, during reduction of a spinal rod into an implant.

Alternatively, in the embodiments shown in FIGS. 4, 5a-5d, 6 and 7a-7f, the rod reducer 44 may have a substantially circular cross section. In the embodiment of FIG. 4, the rod reducer comprises to curved arms 44a', 44b' configured to surround and engage the engagement mechanism 42. A back wall 44c connects the curved arms 44a', 44b' and defines the rod seat 441 on a lower bearing surface 44a thereof. In the embodiments of FIGS. 5a-5d, 6 and 7a-7f, the rod reducer 44 comprises a substantially annular ring 440 encircling the engagement mechanism 42 and including opposed recesses 441a, 441b defining the rod seat 441.

In the embodiment of FIG. 1, the rod seat 441 extends substantially perpendicular to the handles 22, 24, such that a rod 50 engaged by the reducer 44 extends perpendicular to the handles 22, 24. Alternatively, the rod seat 441 extends substantially parallel to the handles 22, 24, so that a rod engaged by the rod reducer 44 extends substantially parallel to the handles 22, 24. One skilled in the art will recognize that the instrument can be designed so that the rod, when engaged by the rod reducer 44, extends at any suitable angle, including intermediate angles between perpendicular and parallel, relative to the handles 22, 24.

The rod reducer 44 may be integrally formed with the second shaft 14 or coupled to the second shaft 14 using any suitable means known in the art. The rod reducer 44 is preferably rigidly connected to the second shaft 14 so that the rod reducer 44 moves with the second shaft when the user actuates the instrument 10.

The implant-engagement mechanism 42 may have any suitable size, configuration and method of operation suitable for engaging and retaining a selected portion of implant that is to receive a rod, such as a head of a polyaxial screw. For example, in the embodiment shown in FIGS. 1-7f, the implant-engagement mechanism 42 comprises a pair of spaced-apart, flexible fingers 42a, 42b or protrusions extending substantially parallel to the linear portion 11. The fingers 42a, 42b cooperate to selectively engage a corresponding portion of a polyaxial screw head.

In the embodiment of FIGS. 1-2d, a first of the flexible fingers 42a aligns with the distal end of the first shaft 12, while the second of the flexible fingers 42b is spaced from the first flexible finger 42a and extends betweens the protrusions 44a, 44b defining the rod reducer 44. A connection ring 421 forms a base for connecting a first end of the second flexible finger 42b to the first end of the first flexible finger 42a, while defining a portion the channel 46 in the inner opening of the ring. The channel 46 further includes the space 461 between the fingers 42a, 42b. The first flexible finger may be integral with or separate from the distal end of the first shaft 12.

Alternatively, as shown in FIGS. 3a-7f, both of the flexible fingers 42a, 42b may be spaced from the linear portion 11 of the instrument.

As shown in FIGS. 1 and 2a-2d, each of the flexible finger components 42a, 42b includes an elongated flexible body, respectively and retractable tabs, pins, ridge or other feature formed on one end. The tabs, pins, ridge or other feature are configured to be inserted into and engage a corresponding feature, such as a recess, bore, slot or ridge of the spinal implant to retain the implant on the instrument 10. For example, the retractable tabs of the illustrative embodiment are configured to engage corresponding recesses on an outer surface of a head portion of a polyaxial screw. Alternatively, each of the tabs or other suitable feature may be formed on an outer surface of the corresponding finger 42a, 42b, respectively, so as to engage corresponding recesses on a different surface of the head portion of the polyaxial screw, for example, an inner wall defining a channel for receiving the rod in the head of the polyaxial screw. The tabs can have any suitable size and shape suitable for insertion into a corresponding recess, bore or slot of a selected implant.

According to one embodiment the tabs on the finger components 42a, 42b form a dovetail feature for mating with a corresponding dovetail feature on the implant, though one skilled in the art will recognize that any suitable means for engaging the implant may be used.

In an illustrative embodiment, the fingers 42a, 42b flex to move the tabs or other feature relative to each other to selectively engage the implant, though one skilled in the art will recognize that any suitable means for engaging the implant may be used in accordance with the teachings of the invention. While the illustrative fingers 42a, 42b are flexible to facilitate selective engagement with an implant, the engagement mechanism 42 is not limited to flexible finger components. For example, in an alternate embodiment, only the second flexible finger 42b is flexible or otherwise movable relative to the first finger 42a, while the first flexible finger 42a, may be substantially rigid. In another embodiment, both fingers 42a, 42b may be rigid and moveable relative to each other to selectively engage and disengage the implant.

The implant-engagement mechanism 42 may be integrally formed with the first shaft 12 or coupled to the first shaft 12 using any suitable means known in the art. The implant-engagement mechanism 42 is preferably rigidly connected to the first shaft 12 so that the implant-engagement mechanism 42 moves with the first shaft when the user actuates the instrument 10.

One skilled in the art will recognize that the engagement mechanism 42 for selectively engaging the implant and securing the implant to the instrument is not limited to the finger component 42a, 42b, and that any suitable device for engaging the implant may be used. The implant engagement mechanism 42 can employ a variety of mating elements, including, but not limited to: tongue-and-groove connections, dovetail connections, and other types of connections known in the art.

According to an illustrative embodiment, the implant-engagement mechanism 42 is locked to a selected implant 52 by squeezing the handle portion 40 to move the rod reducer 44 toward the distal end of the instrument 10. For example, in the embodiment of the invention shown in FIGS. 1-2d, a set of rollers 48 extends between the top of the protrusions 44a, 44b. When the user actuates the instrument 10, for example, by squeezing the handles 22, 24, the rod reducer 44 moves relative to the implant-engagement mechanism 42, causing the rollers 48 to slide over the outer surface of 443b of the second finger 42a. As the rod reducer 44 continues to move relative to the implant engagement mechanism 42, the rollers 48 push the fingers together, causing the tabs to engage and lock into the recesses of the spinal implant. While the rollers 48 are pushed against the lower portion of the second finger 42b, the implant-engagement mechanism 42 is locked to the implant 52.

One skilled in the art will recognize that any suitable means for locking the instrument 10 to a selected implant may be used. For example, in an alternate embodiment, as shown in FIGS. 3a-3e, the protrusions 44a, 44b, or the curved arms 44a', 44b' shown in FIG. 4, of the rod reducer 44 may be configured to abut and latch onto the outer surface of the fingers 42a, 42b. As the rod reducer 44 slides relative to the engagement mechanism, the protrusions 44a, 44b or arms 44a', 44b' slide over the outer surface and squeeze the fingers 42a, 42b into a locking position. Where the rod reducer 44 comprises a ring, as shown in FIGS. 5a-7f, the ring 440 may be sized and configured to compress the fingers 42a, 42b into a locking position as the ring 440 moves from the first position to the second position.

In an alternate embodiment, the implant-locking element is separate from and/or operated independently from the rod reducer 44.

The actuator portion 40 can further include a release mechanism for forcing the engagement mechanism 42 to release the implant, when necessary, for example, after insertion of a rod. For example, as shown in FIGS. 6 and 7a-f, the fingers 42a, 42b can include hooks 70 on outer surfaces thereof. The hooks 70 are configured to allow the rod reducer 44 to easily slide over the hooks when the instrument 10 moves from the first position to the second position. When the user moves the instrument from the second position to the first position, i.e., moving the rod reducer 44 away from the implant-engagement mechanism 42, the rod reducer 44 catches the hooks 70 to force the fingers 42a, 42b apart, releasing the implant 52. One skilled in the art will recognize that any suitable means for ensuring release of the implant can be used, and that a release mechanism, if included, can be separate from and/or operated independently from the rod reducer 44.

In the embodiment of FIGS. 1-4, the channel 46 for inserting and securing a rod-locking mechanism, such as a set-screw, to secure the rod in the implant extends through the connection ring 421 or base 421' of the fingers, through a space 461 defined between the fingers 42a, 42b and a space 462 between the protrusions 44a, 44b of the rod reducer. In the embodiments where the rod reducer 44 comprises a ring 440, the ring 440 includes a central channel 462' aligned with the space between the fingers for the channel 46.

According to one embodiment, as shown in FIGS. 5a-5e, the handle portion 20 may include a proximal channel portion 46a aligned with the channel 46 in the actuator portion 46 for holding a driver for the rod-locking mechanism. As shown, in FIGS. 5c-5e, a driver for the rod-locking mechanism, illustrated as a screwdriver 500 may be inserted through the channel 46 to allow a surgeon to easily insert and/or remove a locking mechanism, such as a setscrew, while maintaining a force on the rod.

The actuation portion 40 of the instrument 10 is not limited to the embodiments described relative to FIGS. 1-7f. One of ordinary skill in the art will recognize that the actuation portion 40 may have any size, shape and configuration suitable for engaging and inserting a spinal rod into a rod-receiving portion of an implant.

The instrument may further include a biasing element, such as a spring, disposed between relatively movable elements to bias the instrument to a default position. The biasing element may be located between the handle members, the shafts 12, 14 and/or the rod reducer and the implant engagement mechanism. For example, FIG. 6 shows a spring 68 between the handles 22, 24 for biasing the handles 22, 24 in a selected position relative to each other.

According to another embodiment, the instrument 10 can include a component for providing additional leverage for forcing the rod into the rod-receiving portion of a selected implant. For example, as shown in FIG. 6, the first handle 22 and first shaft 12 can be pivotally coupled to the second handle 24 and second shaft 24 using a double hinge. The double hinge provides increased mechanical advantage to a user. As the user pulls the first end 24a of the second handle 24 towards the first end of the first handle 22, the second end of the second handle 24 pivots about a first hinge point 60 in the opposite direction. The second end 24b of the handle 24 is pivotally connected to the second shaft 14 about a second hinge point 62, which translates the rotational movement of the second end 24a of the handle 24 about the first hinge point 60 into a linear movement of the second shaft 14 relative to the first shaft 12. The first handle 22 can optionally be pivotally connected to the first shaft 12 through a third pivot point 64 to promote linear movement of the shafts relative to each other. As described, the linear movement of the shafts causes the rod reducer 44 to move towards the distal end of the implant engagement mechanism 42 to insert a rod into an engaged implant. As shown in FIG. 6, the second shaft 14 is inserted through and guided by a channel extending through the first shaft 12. The channel constrains the movement of the second shaft 14 to align with the first shaft 12, facilitating actuation of the actuator portion 40.

Other suitable means for increasing the leverage of the instrument are known in the art and include, but are not limited to, threaded connections, springs, hydraulic pistons, and so on.

The instrument can also include a locking mechanism, such as a ratchet, for selectively locking the instrument in the second, closed position, so that the rod reducer will continue to apply a force to the rod without requiring the user to hold the instrument in the second position. For example, as shown in FIG. 6, the instrument can include a knurled knob 67 for holding the first shaft in a selected position relative to the second shaft. The knob 67 includes male threads configured to mate with female threads on the top of the second shaft 14. The knob 67 is hollow, and rides freely along the second shaft. When the handles 22, 24 are squeezed together, the knob contacts the top of the second shaft. The male threads on the knob 67 mate with the female threads on the second shaft to lock the first shaft in the forward position. The second shaft can contain a shoulder configured to abut the knob 67 to facilitate locking of the instrument in the forward position. The illustrative knob 67 is configured to only engage the female threads when the handles have been squeezed to lock the instrument in a selected position.

One skilled in the art will recognize that any suitable means for selectively locking the instrument in a selected position may be used.

Figure 8A:
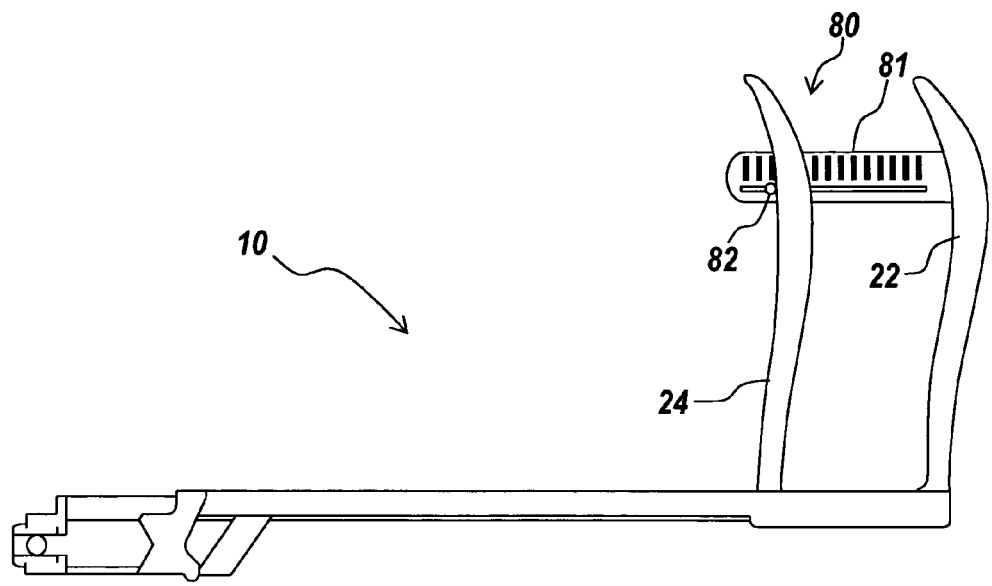
FIGS. 8a and 8b illustrate an instrument for inserting a spinal rod into an implant including a ratchet mechanism, according to another embodiment of the invention
Figure 8B:
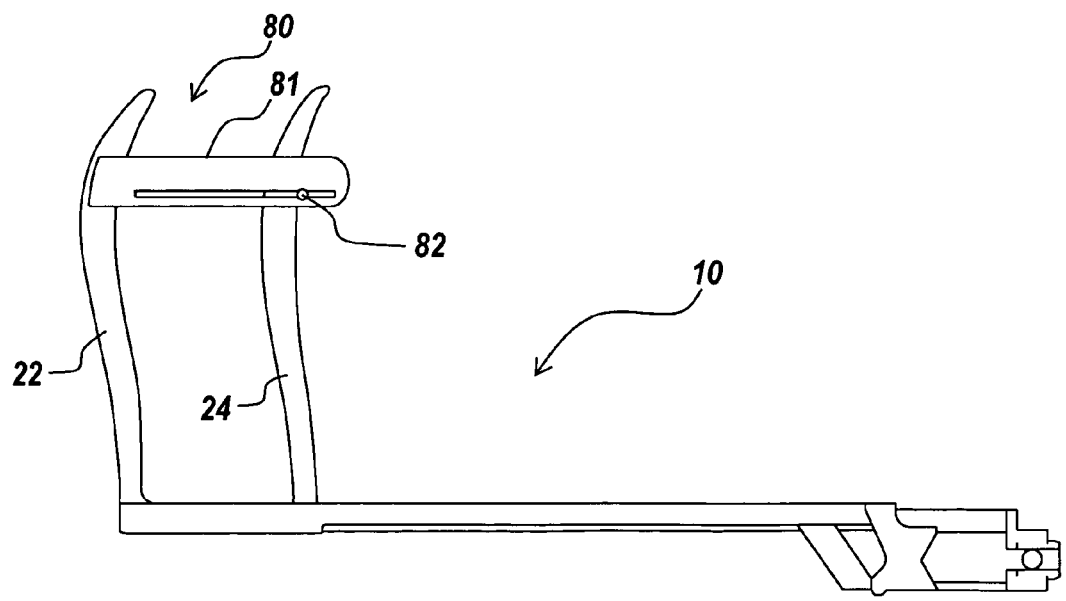

In another embodiment, shown in FIGS. 8A and 8B, the instrument 10 for guiding a rod into an implant can include a ratchet mechanism 80. As shown, the ratchet mechanism 80 includes a rack 81 including a plurality of teeth coupled to the first handle 22 and a pin 82 configured to engage the teeth coupled to the second handle 24. The ratchet mechanism 80 allows a user to incrementally advance and lock the handles 22, 24 relative to each other. In this manner, the instrument 10 can apply a force to the rod without requiring the user to apply manual force to the handles 22, 24.

Figure 9:
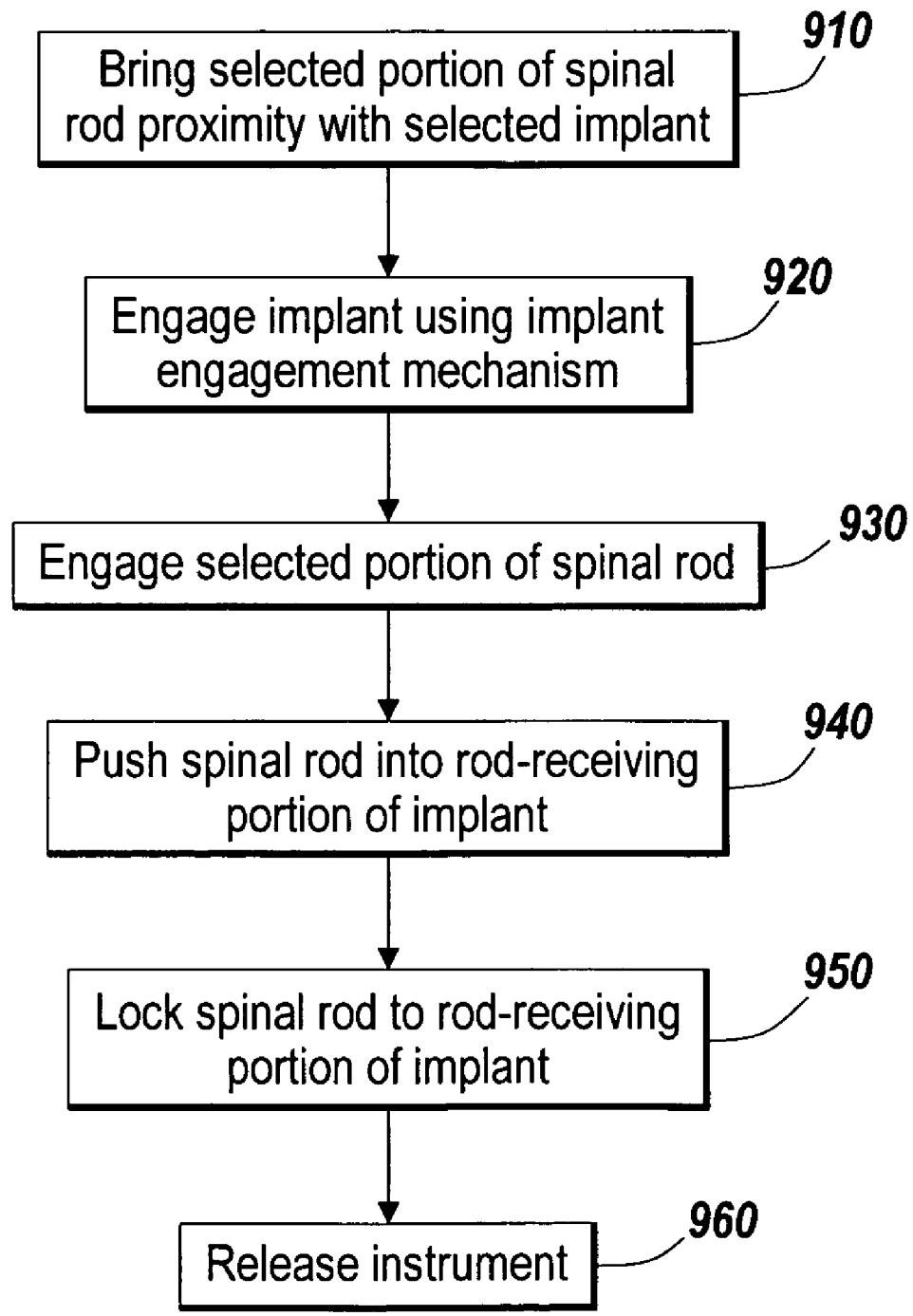
FIG. 9 illustrates the steps involved in inserting a spinal rod into an implant using according to an embodiment of the invention.

FIG. 9 illustrates the steps of inserting and locking a spinal rod to an implant using the instrument 10 according to an illustrative embodiment of the invention. During a spinal surgery, a surgeon screws one or more spinal implants into vertebral bone structures. Typically, the surgeon secures spinal implants to adjacent vertebrae, and then inserts a spinal rod into the rod-receiving portion of each implant to connect the implants. Due to the alignment of the implants, it can be difficult to accurately position the rod within each rod-receiving recess without applying excess force that could potentially damage the spine. The instrument 10 of the present invention facilitates insertion and locking of the rod within a rod-receiving portion.

Figures 3A, 3B:
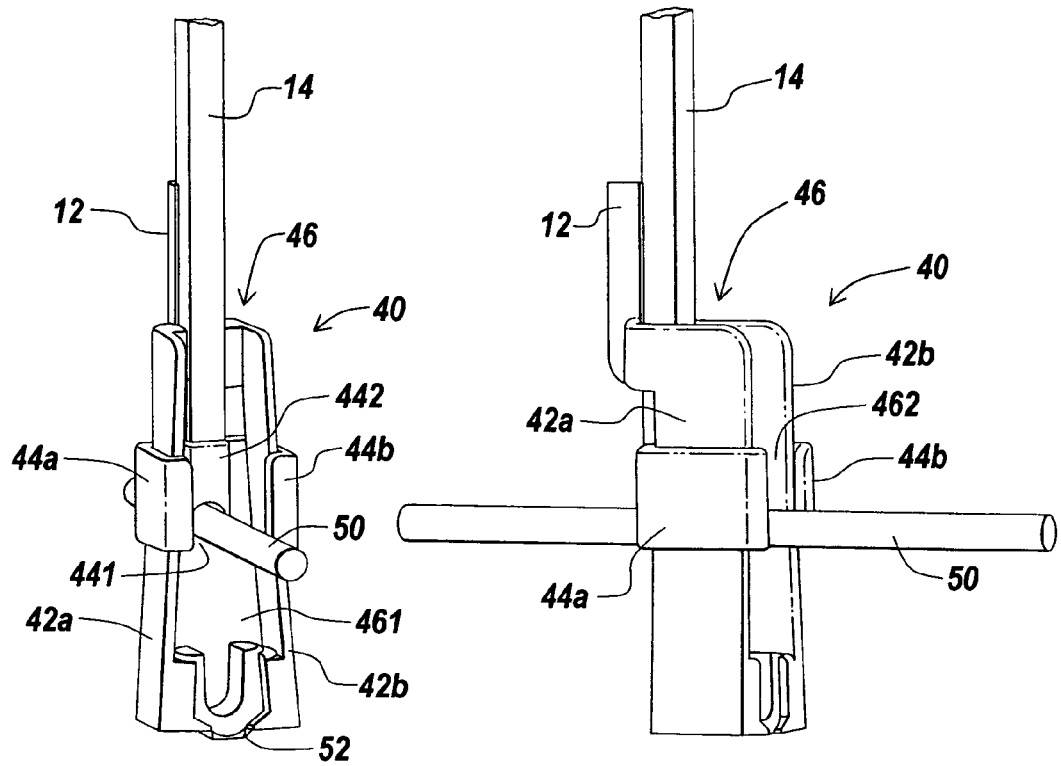
Figure 3C:
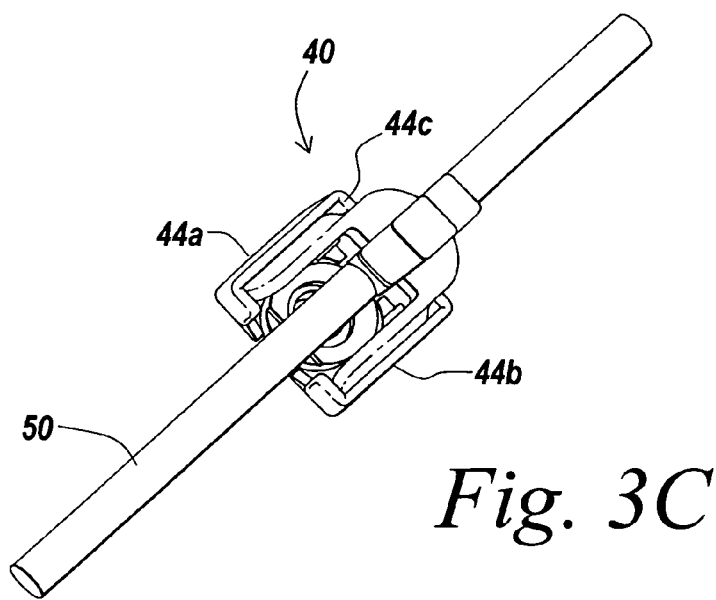
Figure 5A:
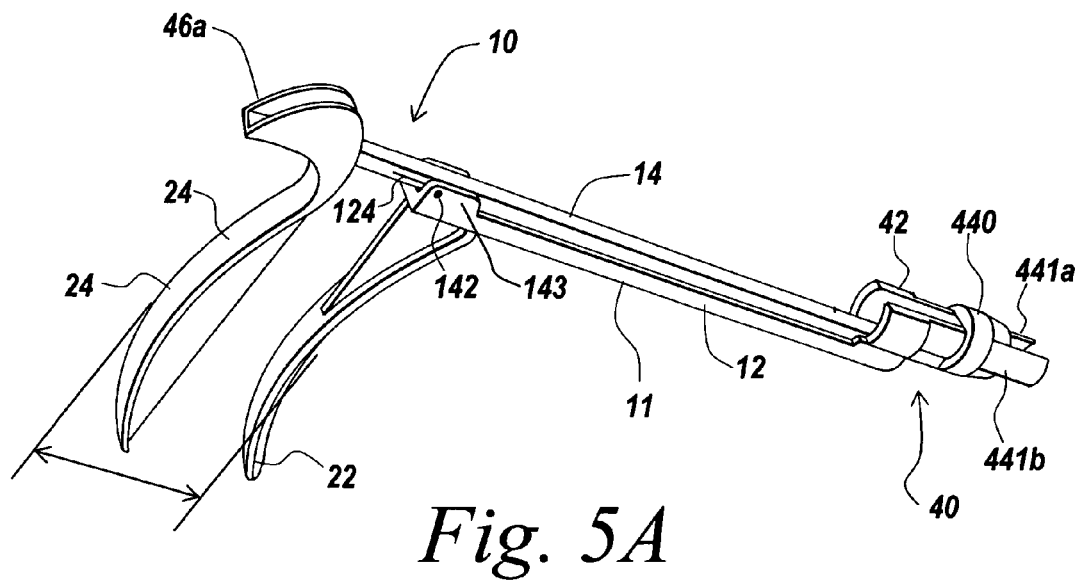
FIGS. 5a-5e illustrate an instrument for inserting a spinal rod into an implant according to another embodiment of the invention.
Figure 5B:
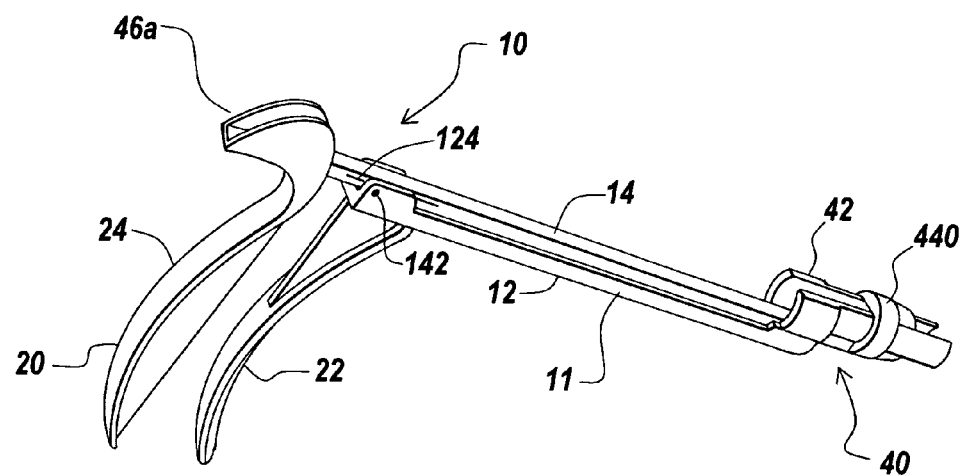
Figure 7A:
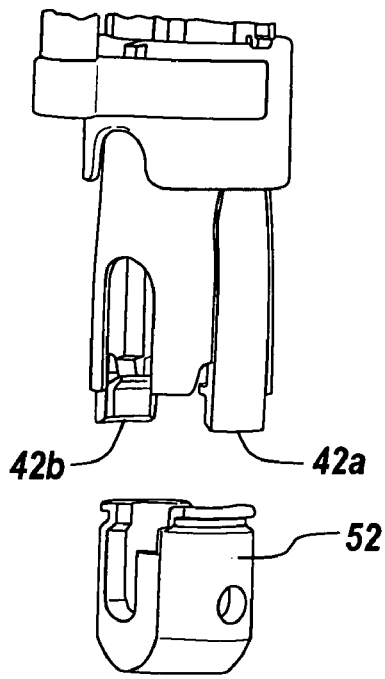
FIGS. 7a-7f are detailed views of the instrument of FIG. 6 during operation of the instrument.
Figure 7B:
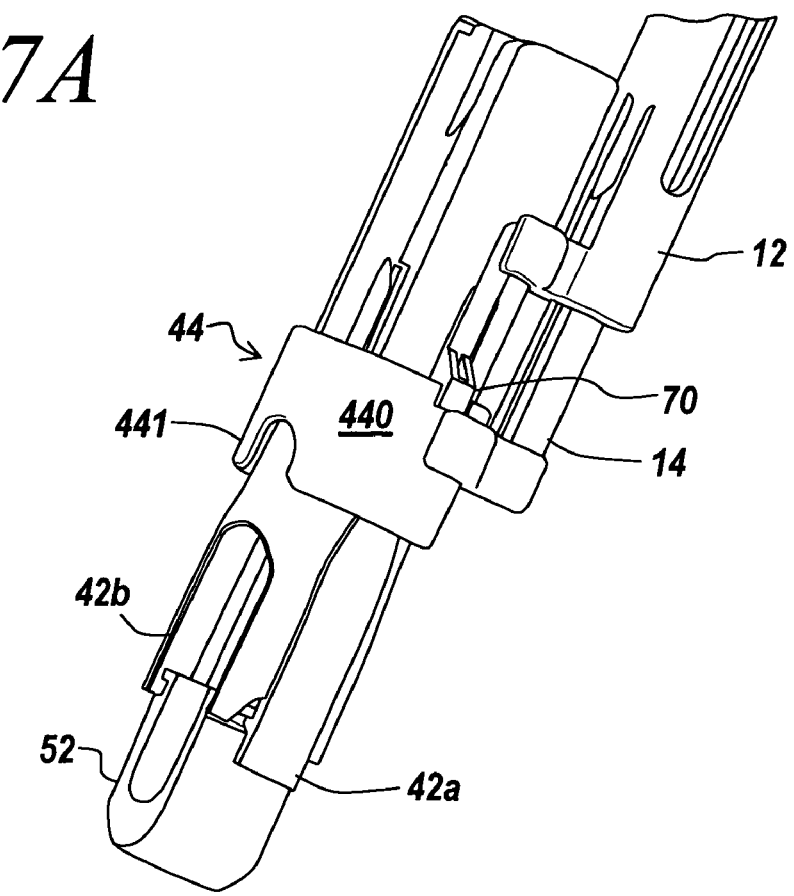
Figure 7C:
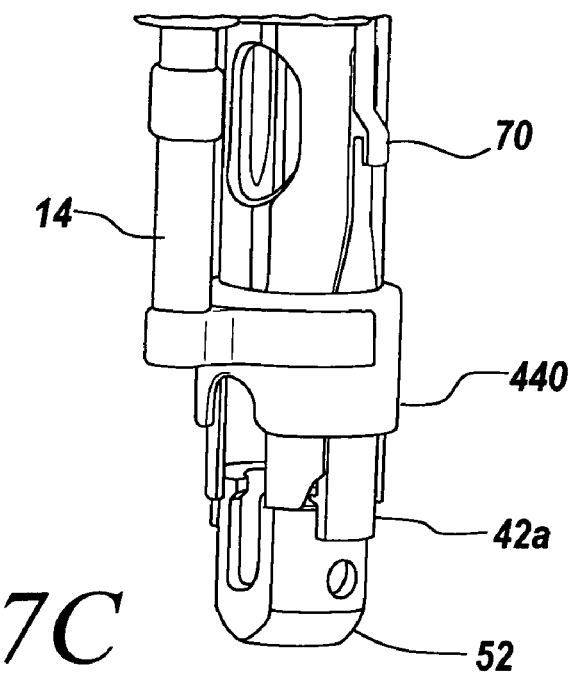
Figure 7D:
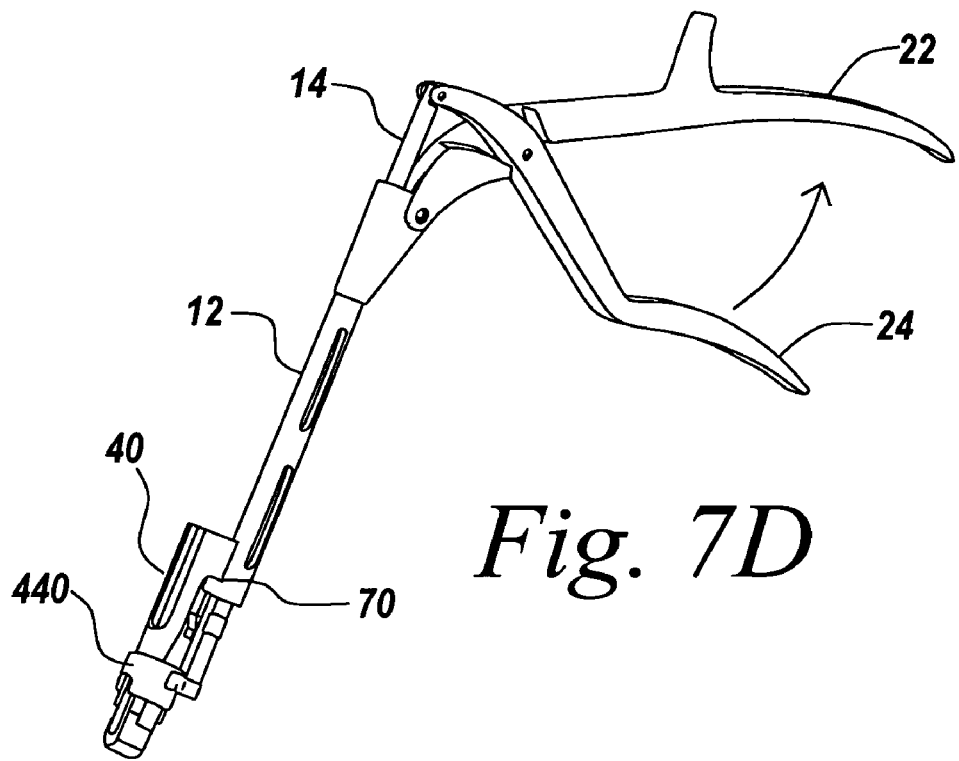
Figure 7E:
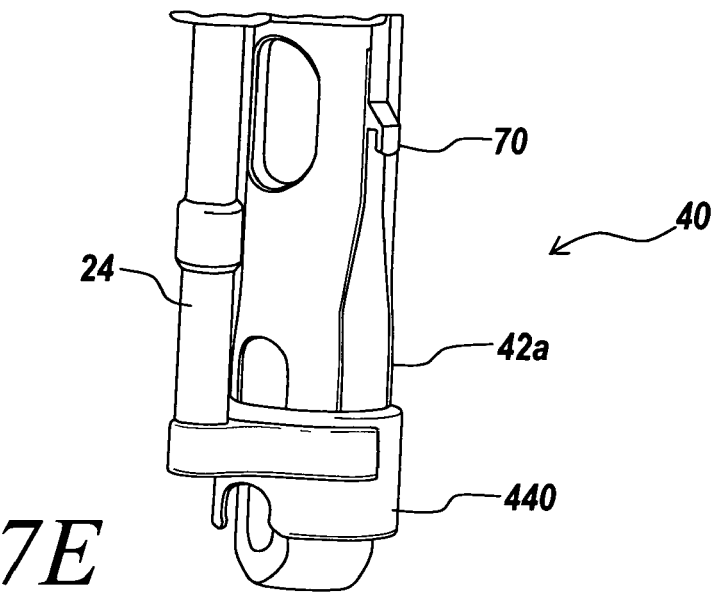
Figure 7F:
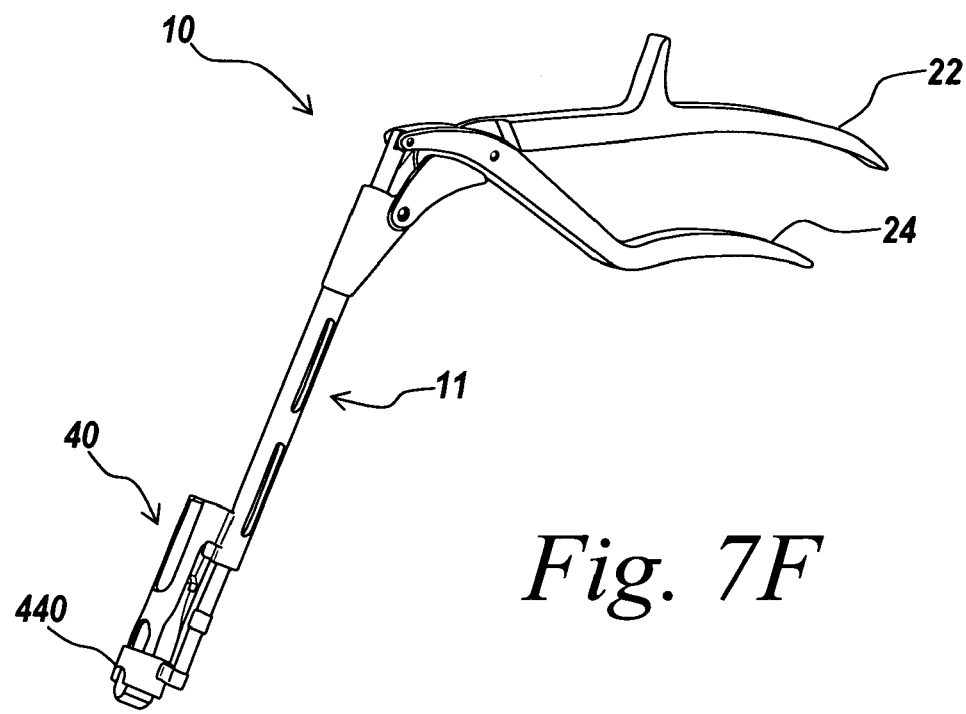

To insert a rod using an instrument 10 of the present invention, a user first selects a portion of the spinal rod to be inserted in the implant and brings that portion into proximity with the implant in step 910. In step 920, the user places the actuator portion 40 of the instrument over the spinal rod, as shown in FIG. 7a, and engages the implant using the implant engagement mechanism 42, as shown in FIG. 7b. In step 920, the instrument 10 is in a first position, with the handles 22, 24 separated from each other, such that the rod reducer 44 and the distal end of the implant engagement mechanism 42 are separate by a predetermined distance. In an illustrative embodiment, the user engages the implant by inserting tabs or protrusions on the fingers of the implant engagement mechanism 42 into corresponding recesses of the head of the implant. In step 930, the user engages the selected portion of the spinal rod by inserting the selected portion into the seat of the rod reducer 44. FIGS. 3a, 3b and 5a illustrate embodiment of the instrument during step 930, when the instrument engages the rod 50 in a first position, spaced from the implant 52 retained by the implant engagement mechanism. In step 940, the user pushes the rod into the rod-receiving portion of the implant. As described above, according to the illustrative embodiment, the user pushes the rod into the implant by compressing the handle portion 20 to bring the first handle and the second handle together, which moves the first shaft relative to the second shaft, such that the first shaft moves toward the handle portion while the second shaft moves toward the actuator portion. The movement causes the rod reducer 44 to move with the second shaft 14 from a first position towards the distal end of the implant engagement mechanism 42 to the second position. As the rod reducer moves towards the distal end, the rod reducer applies a force to and pushes the rod toward the rod-receiving portion of the implant between the fingers of the implant engagement mechanism. FIGS. 4, 5b, 7c and 7d illustrate the instrument 10 during the step of moving the rod reducer 44 towards the distal end of the implant engagement mechanism to bring the rod towards the rod-receiving portion of the implant. The user continues squeezing the handles together until the rod reducer 44 fully pushes the rod into the rod-receiving portion. The step of pushing the rod into the implant may reposition the spine to align with the rod. FIGS. 3d-3f, 5c and 7e-7f illustrate the instrument 10 in the second position after the rod is fully pushed into the rod-receiving portion of the implant and the rod reducer is fully extended.

In one embodiment, the step of inserting the rod by extending the rod reducer simultaneously locks the implant engagement mechanism 42 to the implant 52 by compressing the finger 42a, 42b using the movement of the rod reducer 44 relative to the implant engagement mechanism 42.

Figure 5C:
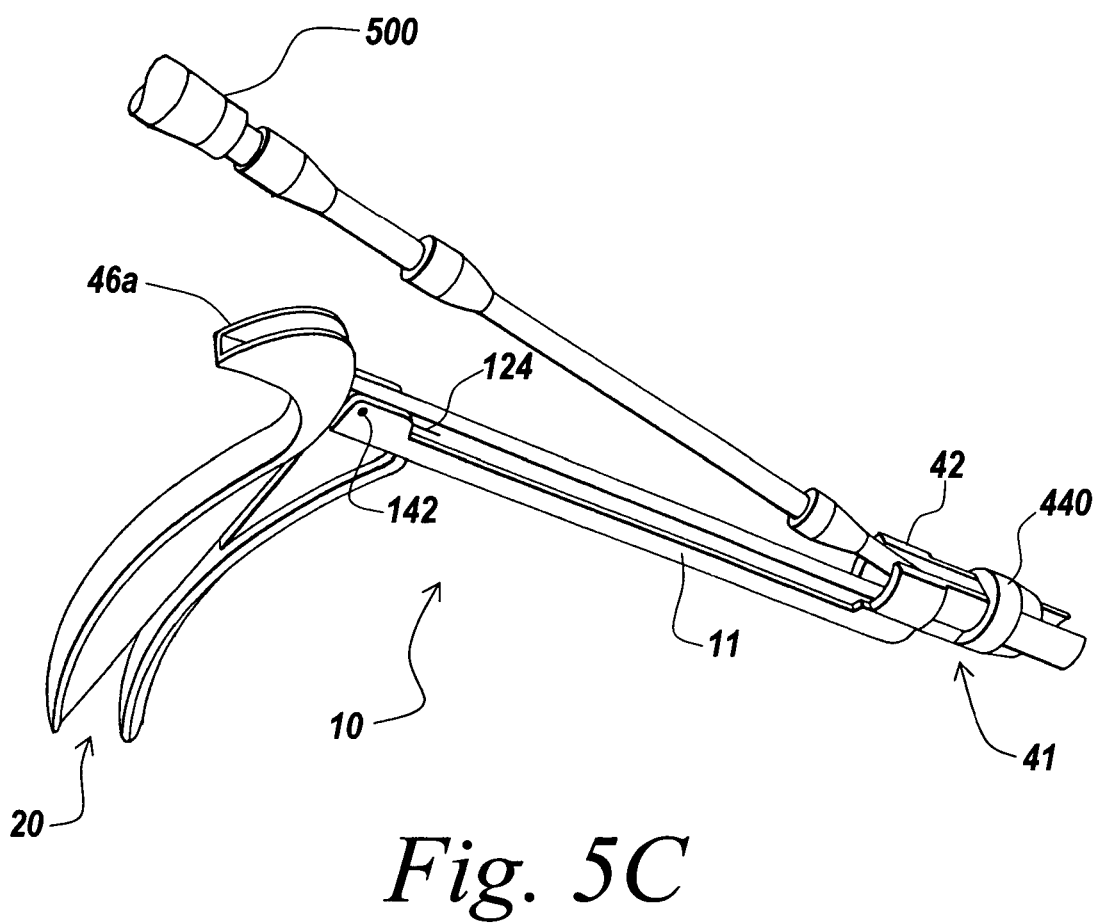
Figure 5D:
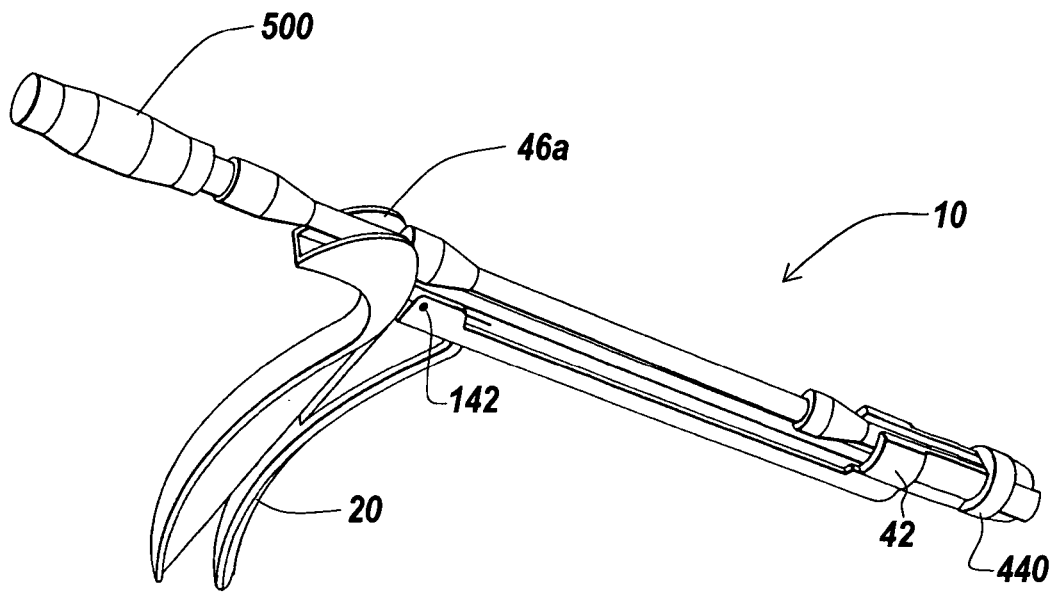
Figure 5E:
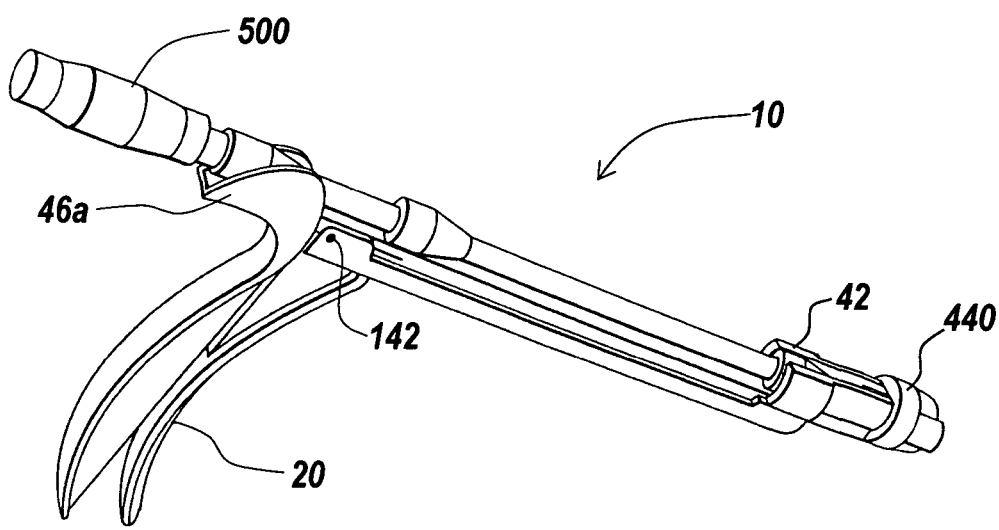

After the rod is placed in the implant, the user locks the rod to the implant in step 950. According to an illustrative embodiment, the user locks the rod to the implant while continuing to apply force to the rod using the rod actuator 44 to keep the rod in the rod-receiving portion. The user inserts a rod-locking mechanism, such as a setscrew into a corresponding portion of the implant via the channel 46. FIGS. 5c-5e illustrate the process of inserting a screw driver 500 for inserting and securing a set screw in the implant while continuing to apply force to retain the rod in the implant.

After inserting and securing the rod, the user can release the one of the handles in step 960 to discontinue the application of force to the rod. In one embodiment, the release of the instrument causes the actuator portion to automatically move away from the implant, under the force of a biasing mechanism. The release of the handle can also cause the implant engagement mechanism to release the implant, allowing the user to easily remove the instrument from the surgical site. For example, as described above, the rod-reducing element 44 can be configured to engage hooks 70 for spreading open the fingers 42a, 42b to release the implant after the user releases the handles.

The present invention provides significant advantages over prior instruments for inserting a spinal rod into an implant. The instrument has a simplified, compact design that provides direct application of force from surgeon's hand onto the rod, without the need for an intermediate linkage system or threaded mechanism. The rod reducer provides direct resistance and tactile feedback to the hand, allowing a surgeon to directly feel resistance being overcome during application of force to the rod. In addition, the instrument includes a channel for inserting a rod-locking mechanism that is aligned with the rod-receiving portion of the implant, allowing the surgeon to apply a balanced force to retain the rod in the rod-receiving portion while locking the rod therein. The channel allows the surgeon to clearly access and view the process of inserting the rod-locking mechanism. The instrument further allows a surgeon to engage an implant and reduce a rod into an implant in the same step, thereby reducing the time involved in performing the rod reduction.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A method of guiding a spinal rod into an implant, comprising the steps of:
   engaging the implant with an implant engagement mechanism coupled to and offset from a first shaft;
   engaging the spinal rod with a rod reducer coupled to and offset from a second shaft slidably mated to the first shaft;
   sliding the first shaft relative to second shaft to cause the rod reducer to push the rod towards a rod-receiving portion of the implant engaged by the implant engagement mechanism; and
   inserting a locking mechanism through a channel defined by the rod reducer and the implant engagement mechanism, wherein the channel is offset from the first shaft and the second shaft.

2. The method of claim 1, wherein the step of sliding locks the implant engagement mechanism to the implant.

3. The method of claim 1, wherein the step of sliding comprises compressing a handle portion connected to the first shaft and second shaft.

4. The method of claim 1, wherein inserting the locking mechanism locks the rod in the rod-receiving portion.

* * * * *

UNITED STATES PATENT AND TRADEMARK OFFICE
CERTIFICATE OF CORRECTION

PATENT NO. : 7,572,281 B2  Page 1 of 1
APPLICATION NO. : 10/913223
DATED : August 11, 2009
INVENTOR(S) : Runco et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1405 days.

Signed and Sealed this

Fourteenth Day of December, 2010

David J. Kappos
*Director of the United States Patent and Trademark Office*